United States Patent [19]

Friebe et al.

[11] Patent Number: 5,925,723
[45] Date of Patent: Jul. 20, 1999

[54] CATALYST/CROSS-LINKING AGENT COMPOSITIONS, A METHOD FOR THEIR PREPARATION AND THEIR USE

[75] Inventors: Robert Friebe; Peter Schwabe; Reiner Voigt, all of Leverkusen, Germany

[73] Assignee: Bayer Aktiengesellschaft, Leverkusen, Germany

[21] Appl. No.: 08/660,308

[22] Filed: Jun. 7, 1996

[30] Foreign Application Priority Data

Jun. 16, 1995 [DE] Germany ............... 195 21 803
Jul. 25, 1995 [DE] Germany ............... 195 27 101

[51] Int. Cl.⁶ .................................................. C08G 77/08
[52] U.S. Cl. .................. 528/18; 523/109; 528/23; 502/153; 502/158
[58] Field of Search ...................... 502/158, 153; 528/18, 23; 523/109

[56] References Cited

U.S. PATENT DOCUMENTS

| | | |
|---|---|---|
| 4,891,400 | 1/1990 | Schwabe et al. . |
| 5,015,413 | 5/1991 | Nagaoka ................. 528/15 |
| 5,047,476 | 9/1991 | Keogh ..................... 525/474 |
| 5,502,144 | 3/1996 | Kuo et al. ............... 528/21 |

FOREIGN PATENT DOCUMENTS

| | | |
|---|---|---|
| 83248 | 8/1969 | German Dem. Rep. . |
| 1104705 | 4/1961 | Germany . |
| 1167527 | 4/1964 | Germany . |
| 2524000 | 12/1976 | Germany . |
| 3544619 | 6/1987 | Germany . |

OTHER PUBLICATIONS

W. Noll, Chemie und Technologie der Silicone, 2nd edition, pp. 339–340, Verlag Chemie, Weinheim, Germany, (1968).

P.J. Smith, Toxicological Data on Organotin Compounds, ITRI Pub. No. 538, International Tin Research Institute, Greenford, Middlesex, U.K., (1979).

International Standard, ISO 4823 2nd edition, (1992).

*Primary Examiner*—Melvyn I. Marquis
*Attorney, Agent, or Firm*—Sprung Kramer Schaefer & Briscoe

[57] ABSTRACT

A catalyst/cross-linking agent composition, containing at least one a) vinyltrialkoxysilane as cross-linking agent,
b) dialkyltin oxide as catalyst,
c) optional organic acid for the control of the reaction time,
d) optional inert solvent, and
e) optional dye or colored pigment, is especially useful for condensation/cross-linking of polysiloxanes, such as OH-endstopped polydimethylsiloxane, in making moldings. Especially useful for impression taking in the dental field.

14 Claims, No Drawings

CATALYST/CROSS-LINKING AGENT COMPOSITIONS, A METHOD FOR THEIR PREPARATION AND THEIR USE

The present invention relates to new catalyst/cross-linking agent compositions, a method for their preparation and their use in condensation cross-linking silicone compounds, in-particular in the field of dentistry.

Silicone compounds are widespread in dentistry as impression materials and are conventionally used in the form of two-component systems. In general the system consists of a silicone polymer based on a polydimethylsiloxane possessing terminal hydroxyl groups, which silicone polymer is mixed with fillers and optionally other auxiliary substances and additives and is obtainable in various consistencies depending upon composition, and of a curing agent component, which is conventionally a conversion product of metal carboxylates, in particular dialkyltin dicarboxylates, and silicate esters in the capacity of a catalyst/cross-linking agent composition.

These two components are homogeneously mixed with one another prior to application and as a result of a polycondensation reaction cross-link at room temperature within 2 to 5 minutes to form a silicone elastomer and small quantities of alcohol, which slowly diffuse out of the material.

The use of organotin compounds or of the conversion products of organotin compounds with silicate esters as catalysts in condensation cross-linking polysiloxane materials was described in detail in the literature, for example, W. Noll, Chemie und Technologie der Silikone, Verlag Chemie, Weinheim, 2nd edition, 1964, pages 339–340. In DAS 1 167 527, DD-B 83 248 and DOS 2 524 000 there are described, for example, conversion products of dialkyltin dicarboxylates with alkoxysilanes. DAS 1 104 705 moreover discloses conversion products of dialkyltin oxides with organosiloxanes and optionally organoalkoxysilanes such as, for example, methyltriethoxysilane. These conversion products may contain organic acids as further additives. The per se good reactivity of these conversion products is, as is known, improved by the addition of such compounds.

Suitable catalyst/cross-linking agent compositions may contain additions of particular isoparaffins, such as 2,2,4,4,6,6,8-heptamethylnonane and 2,2,4,4,6,6,8,8,10-nonamethylundecane (see U.S. Pat. No. 4,891,400 and DOS 35 44 619). These compounds act as solubilizers during the incorporation of the curing agent components into the silicone impression materials, particularly in a liquid form of application, whereby a good homogeneity of the mixed compound is rapidly achieved. Moreover the surface tension of a droplet of a liquid curing agent is also altered in such a way that the dropwise measured addition of the liquid curing agent from a dropping bottle onto a strand of silicone compound is facilitated.

Particular requirements are placed on the properties of these catalyst/cross-linking agent compositions depending on the respective field of application. In the use of these products in dentistry certain requirements relating to technical application, and especially toxicological properties, must be met such as, for example, a high reactivity of the impression material with processing times of 2 to 5 minutes and in addition the shortest possible setting times of from 5 to 6 minutes.

As is known, methoxy-substituted silanes are distinguished from ethoxy-substituted silanes by higher reactivities. Furthermore, following the polycondensation reaction and storage for 24 hours, the cross-inked impression materials exhibit a lower shrinkage owing to the diffusion away of the smaller methanol molecule than they do after the diffusion away of ethanol. Hence a proportion of methoxysilanes in the curing agent component proves to be advantageous both with regard to the reactivity and the dimensional stability of the impression materials, which is indeed an essential precondition for an accurate reproduction. The chemical constitution of the organotin compounds also has an influence on the reactivity of the curing agent component. Thus dibutyltin compounds are more reactive than dioctyltin compounds.

If the toxicological properties of these compounds are compared, however, it is apparent that especially the use of dioctyltin compounds is to be preferred in view of the lower toxicity (see P. J. Smith, Toxicological Data on Organotin Compounds, International Tin Research Institute, Fraser Road, Perivale, Greenford, Middlesex, I.T.R.I. Publication No. 538, 1979):

| | $LD_{50}$ [mg/kg] (oral, rats) |
|---|---|
| $(n\text{-}C_4H_9)_2SnO$ | 487–520 |
| $(n\text{-}C_8H_{17})_2SnO$ | >4000 |
| $(n\text{-}C_4H_9)_2SnCl_2$ | 112–219 |
| $(n\text{-}C_8H_{17})_2SnCl_2$ | >4000 |
| $(n\text{-}C_4H_9)_2Sn(OOCC_{11}H_{23})_2$ | 175 |
| $(n\text{-}C_8H_{17})_2Sn(OOCC_{11}H_{23})_2$ | >6000 |

Another important requirement for the catalyst/cross-linking agent composition in relation to technical application is its stability to activity and in this connection particularly its long-term behavior. The silicate esters and the organotin compounds are conventionally reacted under inert gas atmosphere at elevated temperatures and depending on the reactivity of the product one or the other component is replenished, in order to maintain the required initial reactivity of the curing agent component. In many cases a chemical equilibrium is established within three to six months after preparation and the curing agent component only then has the correct reactivity for the application.

Prior to application, for example, by the dentist the silicone impression materials have to be homogeneously mixed with the curing agent within 30 seconds. The quantity of liquid curing agent used must therefore not be too large and must mix in easily. Secondly, the consistency of the impression material should not alter significantly as a result of the admixture of the curing agent.

The catalyst/cross-linking agent compositions known in the prior art do not fulfil all the set requirements. There existed, therefore, the task of providing suitable catalyst/cross-linking agent compositions, in particular for an application in dentistry, which do not possess the known disadvantages of existing compositions. The catalyst/cross-linking agent compositions should therefore possess a low toxicity, a good reactivity, as far as possible without change from the time of preparation up to use after two to three years, and an alteration in the dimensions of the cross-linked silicone impression materials of less than 1.5%, measured in accordance with DIN 24823 (ISO 4823, Part 7.7).

Surprisingly, it has been found that catalyst/cross-linking agent compositions which contain as essential components vinyltrialkoxysilanes and dialkyltin oxides fulfil virtually all these requirements. The catalyst/cross-linking agent compositions according to the invention are distinguished by a low toxicity, a high reactivity at favorable processing times, rapid setting times and a high dimensional stability of the vulcanized impression materials.

The present invention therefore provides catalyst/cross-linking agent compositions, containing a) at least one vinyltrialkoxysilane as cross-linking agent,
b) at least one dialkyltin oxide as catalyst,
c) optionally an organic acid or a mixture of several acids for the control of the reaction time,
d) optionally inert solvents and
e) optionally dyes and/or colored pigments.

In a preferred embodiment component c) is contained in the catalyst/cross-linking agent composition.

Component a) within the meaning of the invention comprises all currently available vinyltrialkoxysilanes. Here vinyltrialkoxysilanes wherein alkoxy represents $C_1$–$C_6$ alkoxy radicals are preferred.

As vinyltrialkoxysilane a) vinyltrimethoxysilane and/or vinyltriethoxysilane and/or partial hydrolysates thereof are particularly preferred. Small additions of further silicate esters such as, for example, polymethyl silicate, tetramethyl silicate, polyethyl silicate or tetraethyl silicate, may also be present.

Component b) within the meaning of the invention comprises all currently available dialkyltin oxides. Dialkyltin oxides within the meaning of the invention are preferably dialkyltin oxides wherein alkyl represents $C_1$–$C_{12}$ alkyl radicals.

Component b) is particularly preferably dioctyltin oxide (($C_8H_{17}$)$_2$SnO). Dibutyltin oxide or mixtures of dibutyltin oxide and dioctyltin oxide are likewise preferred as component b).

Organic acids c) within the meaning of the invention are preferably aliphatic and aromatic saturated and unsaturated mono- and dicarboxylic acids as well as sulphonic acids. The good reactivity of the curing agent components according to the invention can be improved by the addition of such organic acids. Examples of these organic acids c) are 2-ethylhexanoic acid, benzoic acid, p-toluenesulphonic acid and dodecylsulphonic acid. Benzoic acid is particularly suitable. Additions of these acids moreover produce curing agents particularly stable to activity.

The isoparaffins d) according to the invention are preferably compounds of the general formula

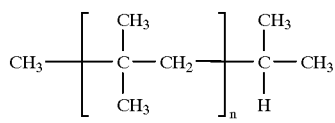

wherein n equals 2, 3, 4 or 5.

It is, of course, possible to use mixtures of isoparaffins. 2,2,4,4,6,6,8-heptamethyl-nonane and/or 2,2,4,4,6,6,8,8,10-nonamethylundecane are particularly preferred as component d).

Dyes and/or colored pigments e) within the meaning of the invention are all dyes or colored pigments known and used in prior art. In the catalyst/cross-linking agent composition according to the invention the dye e) is preferably an inorganic or organic colored pigment or an organic dye. Particularly preferably e) is a dye soluble in fat.

The present invention moreover provides catalyst/cross-linking agent compositions which contain
a) at least one vinyltrialkoxysilane as cross-inking agent,
b) at least one dialkyltin oxide as catalyst,
c) optionally an organic acid or a mixture of several acids for the control of the reaction time,
d) optionally inert solvents,
e) optionally dyes and/or colored pigments and in addition further
f) fillers and/or paraffins and/or Vaseline petroleum jelly and/or waxes and/or polydiorganosiloxanes.

The further additives f) are used in the catalyst/cross-linking agent compositions according to the invention chiefly in order to prepare a paste-like form of application.

The catalyst/cross-linking agent composition according to the invention contains preferably
100 parts by weight of vinyltrialkoxysilane a),
1 to 100 parts by weight of dialkyltin oxide b),
0 to 40 parts by weight of an organic acid c),
0 to 100 parts by weight of an inert solvent d),
0 to 10 parts by weight of dye e),
0 to 300 parts by weight of filler and/or paraffins and/or Vaseline petroleum jelly and/or waxes and/or polydiorganosiloxanes.

The individual components may however also contain several (different) constituents.

The present invention moreover provides catalyst/cross-linking agent compositions obtainable by the reaction of at least one vinyltrialkoxysilane a) and at least one dialkyltin oxide b) and optionally an organic acid c).

The preparation of the conversion products, according to the invention, of organotin compounds with alkoxysilanes usually takes place at elevated temperatures in the range of from 50° C. to 180° C. In the course of this the organotin compound is heated together with the alkoxysilane in a suitable reaction vessel under an inert gas atmosphere, until a clear solution has formed. It has proved advantageous to leave the reaction mixture optionally for several more hours at elevated temperatures. The conversion may optionally be carried out in the presence of an organic acid. Here the acid can be added immediately to components a) and b) and/or added subsequently.

The present invention also provides a method for the preparation of catalyst/cross-linking agent compositions which are free from component f), whereby at least one vinyltrialkoxysilane a) and at least one dialkyltin oxide b) are reacted at temperatures of from 0 to 200° C., preferably of from 20 to 150° C., optionally in the presence of other components, selected from c) to e).

The preparation of the catalyst/cross-linking agent composition according to the invention containing component f) is carried out by current methods. Here component f) is placed in a reeiver and a) and b) and optionally c) to e) are added subsequently with stirring.

The addition of further constituents c), d) and e) according to the invention can be carried out in the course of the reaction at elevated temperatures, also subsequently thereto by incorporation at room temperature.

The present invention also provides the use of the catalyst/cross-linking agent compositions according to the invention in condensation cross-linking silicone materials, for example, in the field of dentistry, impression and casting materials, sealing and coating materials. Particularly preferred is the use in dental impression materials and in applications intended for contact with foodstuffs.

The present invention moreover provides the use of the catalyst/cross-linking agent composition according to the invention in dentistry and in dental technology for the condensation cross-linking of materials based on OH-endstopped polydimethylsiloxanes.

The following examples assist in explaining the invention, but without limitation thereto.

EXAMPLES OF EMBODIMENTS
EXAMPLES

A General description of the preparation of the liquid curing agent

The quantities given in Table I of alkoxysilane a) and of dialkyltin oxide b) and of organic acid c) were placed in a three-necked flask equipped with stirrer, thermometer and reflux condenser and stirred under reflux under a nitrogen atmosphere for about 4 hours at a temperature of about 120° C. Then the organic acid c) was added to the product, if this had not already been done, and the mixture was tested as a curing agent for the impression material described below.

B Preparation of a condensation cross-linking silicone impression material of low viscosity 75 per cent by weight of an OH-endstopped polydimethylsiloxane having a viscosity of 2000 mPas at 23° C., 24.7 per cent by weight of calcium silicate having a specific surface of about 50 m$^2$/g by BET and 0.3 per cent by weight of an organic colored pigment were mixed together in the mixing vessel of a butterfly-stirrer to form a homogeneous impression material. The assessment takes place in accordance with the conditions given under C.

C Test of the reactivity and alteration in dimensions

The tests described below were carried out at 23±1° C. On a mixing block, 6.8 g of the impression material of low viscosity together with 0.26 ml of the liquid curing agent were homogeneously mixed within 30 seconds by means of a spatula. A portion of the mixed material was placed in an aluminum mold of 20 mm internal diameter and 6 mm in height and the surface was made smooth using the spatula. This sample was used for the later determination of the setting time.

The portion of the mixed material remaining on the mixing block was lifted at intervals of 15 seconds and the flow properties of the material were observed. The end of the processing time was reached when the increase in viscosity owing to the cross-linking reaction had progressed so far that the material no longer ran off the spatula. The length of time from the commencement of mixing to the cessation of flow was recorded in the test report as the processing time.

The setting time was determined by a method whereby, on the portion of the material in the aluminum mold described above, one minute after completion of the processing time and at intervals of 15 seconds, using a hardness tester described in DIN 53505, the Shore A hardness was measured until it was constant over three measuring points. 40 minutes after the commencement of mixing the Shore A hardness was again determined as the final value. The setting time was the length of time from the commencement of mixing to the time at which 80% of the final value of the Shore A hardness had been achieved.

The measurement of the dimensional or linear alteration in the materials, consisting of 6.8 g of impression material and 0.26 ml of liquid curing agent, was carried out in accordance with DIN 24823=ISO 4823, Part 7.7.

TABLE 1

Composition and test results of the liquid curing agents

| | Composition of the liquid curing agent | | | | | | Properties of the molding material | | |
|---|---|---|---|---|---|---|---|---|---|
| | Alkoxysilan a) | Wt. % | Tin compound b) | Wt. % | Organic acid c) | Wt. % | Processing time [min] | Setting time [min] | Dimensional alteration [%] |
| 1.[1] | Tetraethoxy-silane | 85.5 | Dibutyltin oxide | 13.2 | 2-Ethyl hexanoic acid | 1.3 | 7.5 | 21 | 1.26 |
| 2.[1] | Tetraethoxy-silane | 84.3 | Dibatyltin oxide | 13.0 | 2-Ethyl hexanoic acid | 2.7 | 13.5 | 27 | 1.43 |
| 3. | Vinyltri-ethoxysilane | 63.1 | Dioctyltin oxide | 36.2 | Benzoic acid | 0.7 | 4 | 13 | 1.01 |
| 4. | Vinyltri-methoxysilane | 63.5 | Dioctyltin oxide | 36.5 | — | — | 2 | 10 | 0.67 |
| 5. | Vinyltri-methoxysilane | 87.4 | Dioctyltin oxide | 12.1 | Benzoic acid | 0.5 | 3 | 9 | 0.82 |
| 6.[2] | Vinyltri-methoxysilane | 67.5 | Dioctyltin oxide | 12.1 | Benzoic acid | 0.4 | 2.8 | 11 | 0.72 |

[1] Comparative experiment
[2] Liquid curing agent contains in addition 20.0 wt. % of 2,2,4,4,6,6,8,8,10-nonamethylundecane It will be understood that the specification and examples are illustrative but not limitative of the present invention and that other embodiments within the spirit and scope of the invention will suggest themselves to those skilled in the art.

We claim:

1. A curing agent composition, obtained by the reaction of at least one vinyltrialkoxysilane a), at least one dialkyltin oxide b) and optionally an organic acid c) at a temperature of 0–200° C.

2. A curing agent composition according to claim 1, wherein the vinyltrialkoxysilane a) is selected from the group consisting of vinyltrimethoxyzilane, vinyltriethoxysilane and partial hydrolyzates thereof.

3. A curing agent composition according to claim 1, wherein the dialkyltin oxide b) is dioctyltin oxide.

4. A curing agent composition according to claim 1, wherein the organic acid c) is at least one aliphatic or aromatic, saturated or unsaturated monocarboxylic, dicarboxylic or sulphonic acid.

5. A curing agent composition according to claim 1, wherein the organic acid c) is benzoic acid.

6. In the cross-linking of a polysiloxane having terminal —OH groups by a condensation reaction in the presence of a curing agent, the improvement wherein said curing agent is a composition according to claim 1.

7. The method according to claim 6, wherein the polysiloxane being cross-linked by a condensation reaction is an OH-endstopped polydimethylsiloxane.

8. The method for the preparation of a curing agent composition, comprising reacting at least one vinyltrialkoxysilane a) and at least one dialkyltin oxide b) at a temperature from about 0 to 200° C., optionally in the presence of one or more of c) an organic acid for the control of the reaction time,
  d) an inert solvent,
  e) a dye or colored pigment.

9. A curing agent composition according to claim 1, wherein the inert solvent d) is an isoparaffin of the formula

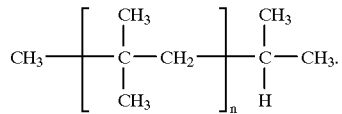

10. A curing agent according to claim 1, wherein 100 parts of vinyltrialkoxysilane a) is reacted with 1–100 parts of tin oxide b) and 0–40 parts of organic acid c).

11. A curing agent according to claim 10, further comprising 0 to 100 parts of inert solvent d), and
  0 to 10 parts of dye e).

12. A curing agent composition according to claim 11, wherein the vinyltrialkoxysilane a) is at least one member of the group consisting of vinyltrimethyoxysilane, vinyltriethoxysilane and partial hydrolyzates thereof, the dialkyltin oxide b) is dioctyltin oxide, the organic acid c) is benzoic acid, the inert solvent d) is an isoparaffin of the formula

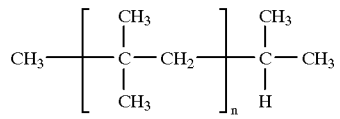

wherein n is 2, 3, 4 or 5, and the dye e) is an inorganic or organic colored pigment or an organic dye.

13. A method of preparing a dental impression which comprises forming a composition comprising a polysiloxane having terminal hydroxyl groups and a curing composition of claim 1, taking a dental impression with said composition and then curing said impression.

14. A curing agent composition according to claim 1, further comprising a pigment or an organic dye.

* * * * *

UNITED STATES PATENT AND TRADEMARK OFFICE
CERTIFICATE OF CORRECTION

PATENT NO : 5,925,723
DATED : July 20, 1999
INVENTOR(S): Robert FRIEBE, et al.

It is certified that error appears in the above-identified patent and that said Letters Patent is hereby corrected as shown below:

Column 7, line 15,   after "the formula" insert
--wherein n is 2, 3, 4, or 5.--

Column 7, line 17,   cancel "tin" and substitute --dialkyltin--

Signed and Sealed this

Twenty-eighth Day of December, 1999

Attest:

Q. TODD DICKINSON

Attesting Officer   Acting Commissioner of Patents and Trademarks